US010566425B2

(12) United States Patent
White et al.

(10) Patent No.: US 10,566,425 B2
(45) Date of Patent: Feb. 18, 2020

(54) APPARATUS COMPRISING A SENSOR ARRANGEMENT AND ASSOCIATED FABRICATION METHODS

(71) Applicant: EMBERION OY, Espoo (FI)

(72) Inventors: Richard White, Huntingdon (GB); Mark Allen, Great Cambourne (GB)

(73) Assignee: EMBERION OY, Espoo (FI)

( * ) Notice: Subject to any disclaimer, the term of this patent is extended or adjusted under 35 U.S.C. 154(b) by 0 days.

(21) Appl. No.: 15/558,237

(22) PCT Filed: Mar. 2, 2016

(86) PCT No.: PCT/FI2016/050128
§ 371 (c)(1),
(2) Date: Sep. 14, 2017

(87) PCT Pub. No.: WO2016/146884
PCT Pub. Date: Sep. 22, 2016

(65) Prior Publication Data
US 2018/0047814 A1  Feb. 15, 2018

(30) Foreign Application Priority Data
Mar. 18, 2015 (EP) .................................. 15159721

(51) Int. Cl.
*H01L 29/16* (2006.01)
*H01L 29/417* (2006.01)
(Continued)

(52) U.S. Cl.
CPC .... *H01L 29/1606* (2013.01); *H01L 27/14634* (2013.01); *H01L 27/14636* (2013.01);
(Continued)

(58) Field of Classification Search
CPC ......... H01L 29/41775; H01L 29/41758; H01L 29/41725; H01L 27/14601;
(Continued)

(56) References Cited
U.S. PATENT DOCUMENTS

| | | | | |
|---|---|---|---|---|
| 2002/0075249 A1* | 6/2002 | Kubota | ................ | G09G 3/2011 345/204 |
| 2005/0127357 A1* | 6/2005 | Wong | ...................... | H01L 27/12 257/59 |

(Continued)

FOREIGN PATENT DOCUMENTS

| | | |
|---|---|---|
| EP | 1 310 999 A2 | 5/2003 |
| EP | 2 341 542 A2 | 7/2011 |

(Continued)

OTHER PUBLICATIONS

International Search Report & Written Opinion dated Jun. 8, 2016 corresponding to International Patent Application No. PCT/FI2016/050128.

(Continued)

*Primary Examiner* — Frederick B Hargrove
(74) *Attorney, Agent, or Firm* — Squire Patton Boggs (US) LLP

(57) ABSTRACT

An apparatus comprising: a plurality of sensors (501) arranged in an array (500), each sensor having a source electrode (504), a drain electrode (503), a gate electrode (505) and a channel, wherein the source electrode and drain electrode are elongate and the channel has a channel width defined by the longitudinal extent of the source and/or drain electrode and a channel length defined by the separation between the source and drain electrodes; a common conductive or semiconductive layer (506), which may be made of graphene, comprising the channels of the sensors (501) and arranged to extend over the plurality of sensors of the array and configured to be in electrical contact with at least (Continued)

the source electrode and the drain electrode of each sensor; and wherein the source electrode or drain electrode of each sensor forms a substantially continuous sensor perimeter at least along the channel width, which substantially encloses the other electrode of each sensor to inhibit the flow of charge carriers beyond the sensor perimeter to inhibit crosstalk between sensors in the array.

13 Claims, 10 Drawing Sheets

(51) Int. Cl.
| | |
|---|---|
| H01L 27/146 | (2006.01) |
| H01L 29/423 | (2006.01) |
| H01L 29/778 | (2006.01) |
| H01L 27/16 | (2006.01) |
| H01L 27/20 | (2006.01) |
| H01L 27/28 | (2006.01) |
| H01L 31/028 | (2006.01) |
| H01L 31/032 | (2006.01) |
| H01L 31/0352 | (2006.01) |
| H01L 31/113 | (2006.01) |
| H01L 31/18 | (2006.01) |
| H01L 37/02 | (2006.01) |
| H01L 41/113 | (2006.01) |
| H01L 41/314 | (2013.01) |
| G01N 27/414 | (2006.01) |

(52) U.S. Cl.
CPC .. *H01L 27/14645* (2013.01); *H01L 27/14658* (2013.01); *H01L 27/14676* (2013.01); *H01L 27/16* (2013.01); *H01L 27/20* (2013.01); *H01L 27/283* (2013.01); *H01L 29/41733* (2013.01); *H01L 29/41758* (2013.01); *H01L 29/4238* (2013.01); *H01L 29/778* (2013.01); *H01L 29/7781* (2013.01); *H01L 31/028* (2013.01); *H01L 31/0324* (2013.01); *H01L 31/035218* (2013.01); *H01L 31/1136* (2013.01); *H01L 31/1804* (2013.01); *H01L 37/02* (2013.01); *H01L 41/1132* (2013.01); *H01L 41/314* (2013.01); *G01N 27/4148* (2013.01)

(58) Field of Classification Search
CPC ......... H01L 27/14649; H01L 27/14658; H01L 29/42392; H01L 27/1214–27/1296
See application file for complete search history.

(56) References Cited

U.S. PATENT DOCUMENTS

| | | | | |
|---|---|---|---|---|
| 2011/0156114 | A1* | 6/2011 | Park | H01L 27/14603 257/294 |
| 2011/0315949 | A1* | 12/2011 | Voutilainen | H01L 27/14621 257/9 |
| 2014/0332757 | A1 | 11/2014 | Kvouris et al. | |
| 2016/0020280 | A1* | 1/2016 | Heo | H01L 33/26 257/27 |
| 2016/0155768 | A1* | 6/2016 | Yi | H01L 27/14643 250/208.1 |
| 2016/0313458 | A1* | 10/2016 | Masuda | G01T 1/247 |

FOREIGN PATENT DOCUMENTS

| | | |
|---|---|---|
| JP | 8-148688 A | 6/1996 |
| JP | 2003-332552 A | 11/2003 |
| JP | 2010-129881 A | 6/2010 |
| JP | 2012-53050 A | 3/2012 |
| JP | 2012-212877 A | 11/2012 |
| WO | WO 2011/161305 A1 | 12/2011 |
| WO | WO 2012/145247 A1 | 10/2012 |
| WO | WO 2013/085715 A1 | 6/2013 |
| WO | 2014/162055 A1 | 10/2014 |
| WO | 2015/012186 A1 | 3/2017 |
| WO | 2015/015700 A1 | 3/2017 |

OTHER PUBLICATIONS

European Search Report dated Sep. 23, 2015 corresponding to European Patent Application No. 15 15 9721.
Jiahua Zhu et al., "An overview of the engineered graphene nanostructures and nanocomposites," RSC Advances, vol. 3, No. 45, Jan. 1, 2013, pp. 22790, XP055212527.
Thomas Mueller et al., "Graphene photodetectors for high-speed optical communications," Nature Photonics, Nature Publishing Group, vol. 4, May 1, 2010, pp. 297-301, XP002639966.
Japanese Office Action issued in corresponding Japanese Patent Application No. 2017-549073 dated Aug. 23, 2018.

* cited by examiner

Figure 14
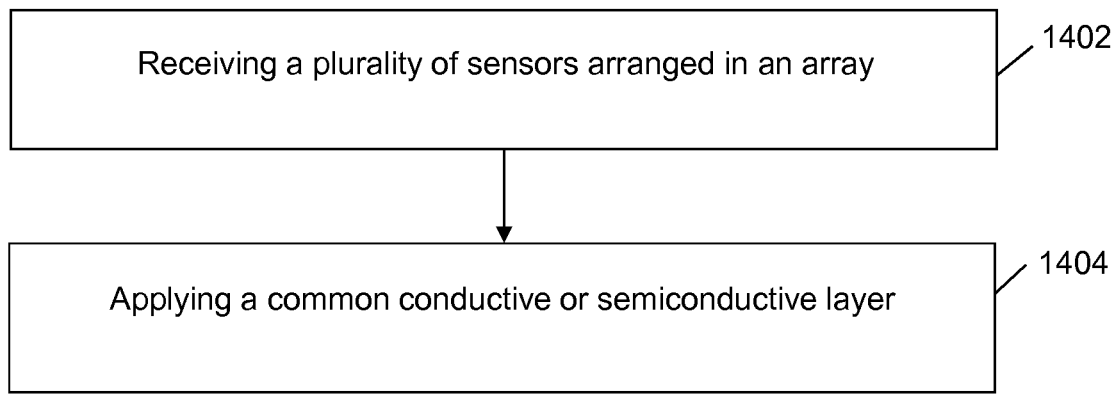
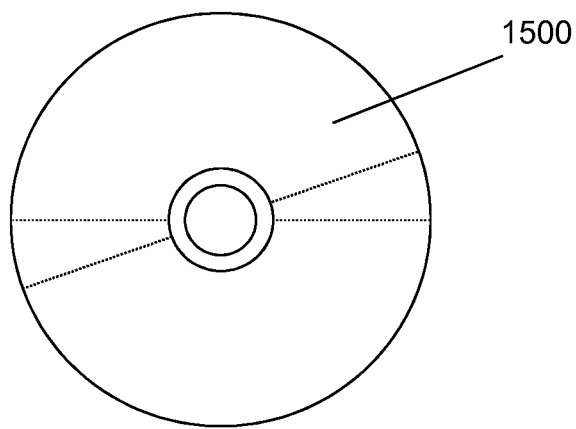
Figure 15

APPARATUS COMPRISING A SENSOR ARRANGEMENT AND ASSOCIATED FABRICATION METHODS

TECHNICAL FIELD

The present disclosure relates to the field of electronic devices and sensors, associated methods and apparatus. Certain disclosed aspects/examples relate to portable electronic devices, in particular, so-called hand-portable electronic devices which may be hand-held in use (although they may be placed in a cradle in use). Such hand-portable electronic devices include mobile telephones, so-called Personal Digital Assistants (PDAs), smartphones and other smart devices, and tablet PCs.

The portable electronic devices/apparatus according to one or more disclosed aspects/embodiments may provide one or more audio/text/video communication functions (e.g. tele-communication, video-communication, and/or text transmission (Short Message Service (SMS)/Multimedia Message Service (MMS)/e-mailing) functions), interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture functions (e.g. using a (e.g. in-built) digital camera), and gaming functions.

BACKGROUND

Two dimensional materials, such as graphene, can be used in the field of electronic devices and sensors. Two dimensional materials may be easily damaged which can lead to a reduction in the integrity of the resulting devices or sensors. It is therefore desirable to apply as few processing or treatment stages after the incorporation of a two dimensional material into a device or sensor as possible.

The listing or discussion of a prior-published document or any background in this specification should not necessarily be taken as an acknowledgement that the document or background is part of the state of the art or is common general knowledge. One or more aspects/examples of the present disclosure may or may not address one or more of the background issues.

SUMMARY

According to a first aspect, there is provided an apparatus comprising:
a plurality of sensors arranged in an array,
  each sensor having a source electrode, a drain electrode and a channel, one of the source and the drain electrodes configured to receive a flow of charge carriers for injecting into the channel and the other configured to provide a current sink for said flow of charge carriers from the channel, wherein the source electrode and drain electrode are elongate and the channel has a channel width defined by the longitudinal extent of the source and/or drain electrode and a channel length defined by the separation between the source and drain electrodes;
  a common conductive or semiconductive layer arranged to extend over the plurality of sensors of the array and configured to be in electrical contact with at least the source electrode and the drain electrode of each sensor; and
wherein the source electrode or drain electrode of each sensor forms a substantially continuous sensor perimeter at least along the channel width which substantially encloses the other electrode of each sensor to inhibit the flow of charge carriers beyond the sensor perimeter to inhibit crosstalk between sensors in the array.

The common conductive or semiconductive layer may be associated with a functional transducer layer for electrically interacting with the common conductive layer in response to a stimulus. In other examples, the common conductive or semiconductive layer is not associated with a functional transducer layer and may be sensitive to particular stimuli itself.

Each sensor may include a gate electrode arranged for modulating the conductivity of the channel between the drain electrode and the source electrode. A dielectric material may be interposed between the gate electrode and the common conductive or semiconductive layer.

The gate electrode may enclose the drain electrode or the source electrode.

The source electrode may be arranged as a common source electrode for all sensors in the array. The drain electrode may be arranged as a common drain electrode for all sensors in the array. The source electrode or the drain electrode may be arranged as a grid configured to define the perimeter of each sensor in the array.

The arrangement of the source electrode, the gate electrode and the drain electrode of each sensor in the array may form a field effect transistor or a field effect transducer (FET).

The sensors may be formed in a substrate. The common conductive layer may be located on a first side of the substrate and a second side of the substrate, opposed to the first side, may be associated with read-out circuitry for reading the output of the sensors in the array.

The sensors may be formed on a substrate and the common conductive layer is located on one side of the substrate and read-out circuitry, for reading the output of the sensors in the array, may be at least one of;
  arranged on a second side of the substrate, opposed to the first side, and interconnected to the sensors via through-vias; or
  arranged embedded in the substrate below the sensors and connected to the sensor electrodes; or
  arranged on a separate substrate and connected to the sensor array by electrical connections.

The read-out circuitry may be configured to control the voltage applied to the gate electrode, which may be used to set an operating point of the sensors.

The electrical connections may extend from the second side of the substrate to the read-out circuitry. The electrical connections may connect each sensor (e.g. FET) to the read-out circuitry. The electrical connections may be vias and/or bondwires.

The common conductive or semiconductive layer may be continuous and substantially unpatterned across the plurality of sensors.

The common conductive or semiconductive layer may comprise a thin-film material. The thin-film material may be less than ten micrometres thick. The thin-film material may be less than one micrometre thick. The thin-film material may be less than one hundred nanometres thick. The thin-film material may be less than ten nanometres thick. The thin-film material may be less than one nanometre thick.

The common conductive or semiconductive layer may comprise a two dimensional material selected from:
  a single layer of a two dimensional material;

a bilayer of a two dimensional material;
a plurality of layers of a two dimensional material.

The common conductive or semiconductive layer, or two-dimensional material, may be graphene.

The functional transducer layer may be selected from:
a layer of conductive or semiconductor nanocrystals;
a piezoelectric material;
a layer of colloidal quantum dots such as Lead sulphide (PbS) quantum dots encapsulated with ligands such as oleate ligands or bidentate ligands of ethanedithiol or pyridine;
a pyro electric film; or
a biochemical species.

The source electrode may include a perimeter portion and at least one finger portion, the finger portion extending inwardly from the perimeter portion; wherein
for at least one of the sensors of the array, the drain electrode and the gate electrode of said at least one sensor are arranged to form at least one finger portion which is interdigitated with the at least one finger portion of the source electrode.

The read-out circuitry may be configured to determine sensed values from one, some of, or each of the sensors of the array. The read out circuitry may be configured to detect the sensed value of each sensor in the array using measurements of an electrical parameter of the source electrode and the drain electrode. The electrical parameter may be the voltage between the source and the drain electrode or the electrical current flowing between the drain electrode and the source electrode.

A first sense electrode may extend between the gate electrode and the drain electrode. The read-out circuitry may be configured to detect a sensed value of one, some of or each sensor using measurements of one or more electrical parameters from the source electrode, the drain electrode and the first sense electrode.

A first sense electrode may extend between the source electrode and the gate electrode and a second sense electrode may extend between the gate electrode and the drain electrode, spaced from the first sense electrode in the channel. Read out circuitry may be configured to detect a sensed value of one, some of or each sensor using measurements of one or more electrical parameters from the source electrode, the drain electrode, the first sense electrode and the second sense electrode for each sensor. This may allow the extraction of the sensor element resistance from the total drain-source resistance, which typically includes the contact resistances, which can be significantly large and can be voltage dependent or dependent of other measures than what we are trying to sense.

The first sense electrode may be in electrical contact with the conductive or semiconductive layer. The second sense electrode may be in electrical contact with the conductive or semiconductive layer.

The read-out circuitry may be configured to energise and read each sensor sequentially.

The read-out circuitry may be configured to energise the sensors simultaneously and read out the electrical parameter associated with each sensor in turn, in groups or simultaneously.

A storage capacitor may be connected in series between the first sense electrode and a reference electrode, such as ground. A storage capacitor may be connected in series between the second sense electrode and a reference electrode, such as ground. The storage capacitors may be configured to store sensed values.

The read-out circuitry may be configured such that a storage capacitor may be connected in series between the first sense electrode and the second sense electrode during the storage phase, then disconnected from the first and second sense electrodes and then connected to a reference electrode, such as ground, during the readout phase.

The storage capacitors may be configured to be read-out by activating switching transistors driven by row and column signals.

Throughout the present specification, descriptors relating to relative orientation and position, such as "top", "bottom", "upper", "lower", "above" and "below", as well as any adjective and adverb derivatives thereof, are used in the sense of the orientation of the apparatus as presented in the drawings. However, such descriptors are not intended to be in any way limiting to an intended use of the described or claimed invention.

The elongate source electrode and the elongate drain electrode may be arranged in a meandering pattern. The sensor elements may be arranged in a grid of rows and columns and wherein sensor elements in a common row have a substantially identical layout and wherein sensor elements in a row adjacent to the common row have a layout substantially a mirror image of the sensor elements in the common row.

The electrodes of each sensor element may face, at the sensor perimeter, a corresponding electrode of an adjacent sensor element. Accordingly, portions of the sensor perimeter that face an adjacent sensor element may be at substantially the same potential as a directly facing portion of the sensor perimeter of the adjacent sensor element.

Each sensor element may include a sensing portion and a reference portion and the read-out circuitry may be configured to, during a sample step, measure an electrical parameter of the sensing portion using a first capacitor and an electrical parameter of the reference portion using a second capacitor, and, during a read-out step, the values stored by the first and second capacitors are read.

The source electrode may be couplable to a lower potential than the drain electrode in use. The source electrode may form a perimeter along the channel length and the channel width.

According to a further aspect, there is provided a method for forming an apparatus comprising:
receiving a plurality of sensors arranged in an array, each sensor having a source electrode, a drain electrode and a channel, one of the source and the drain electrodes configured to receive a flow of charge carriers for injecting into the channel and the other configured to provide a current sink for said flow of charge carriers from the channel, wherein the source electrode and drain electrode are elongate and the channel has a channel width defined by the longitudinal extent of the source and/or drain electrode and a channel length defined by the separation between the source and drain electrodes;
applying a common conductive or semiconductive layer arranged to extend over the plurality of sensors of the array and configured to be in electrical contact with at least the source electrode and the drain electrode of each sensor; and wherein the source electrode or drain electrode of each sensor forms a substantially continuous sensor perimeter at least along the channel width which substantially encloses the other electrode of each sensor to inhibit the flow of charge carriers beyond the sensor perimeter to inhibit crosstalk between sensors in the array.

Following the step of applying the conductive or semiconductive layer, the method may comprise:
  applying a functional transducer layer to the common conductive or semiconductive layer.

The method may include a step of applying a dielectric material to a gate electrode of each sensor in the array prior to applying the common conductive or semiconductive layer.

The step of receiving a plurality of sensors arranged in an array may include:
  forming the source electrode or drain electrode as a common source or drain electrode for all sensors in the array.

The step of receiving a plurality of sensors arranged in an array may include:
  arranging the source electrode or drain electrode as a grid configured to define the perimeters of each sensor in the array.

The step of receiving a plurality of sensors arranged in an array may include:
  arranging the source electrode, the gate electrode and the drain electrode of each sensor in the array to form a field effect transducer/transistor (FET).

The steps of receiving a plurality of sensors arranged in an array and applying a common conductive or semiconductive layer may include:
  optionally, providing read-out circuitry for reading the output of the sensor elements in the sensor array;
  forming the sensors in a substrate; and
  applying the common conductive layer on one side of the substrate.

Forming the sensors in the substrate may include doping a semiconductor substrate and metalizing the substrate to define the source and drain and gate electrodes in a particular layout as described herein.

The step of receiving a plurality of sensors arranged in an array may include:
  forming electrical connections which extend from a surface of the substrate to the read-out circuitry.

The step of receiving a plurality of sensors arranged in an array may include:
  connecting each sensor to the read-out circuitry using electrical connections, such as vias.

The step of applying a common conductive or semiconductive layer may include:
  applying the common conductive or semiconductive layer such that it is continuous and substantially unpatterned across the plurality of sensors.

The common conductive or semiconductive layer may comprise a thin-film material.

The step of applying a common conductive or semiconductive layer may include:
  applying a single layer of a two dimensional material;
  applying a bilayer of a two dimensional material; or
  applying a plurality of layers of a two dimensional material.

The step of applying a common conductive or semiconductive layer may include:
  applying a common conductive layer of graphene.

The step of applying a functional transducer layer may comprise any one of applying:
  a layer of colloidal quantum dots such as lead sulphide (PbS) quantum dots encapsulated with ligands such as for example oleate ligands or bidentate ligands of ethanedithiol or pyridine
  a layer of conductor or semiconductor nanocrystals (such as PbSe, PbTe, CdS, CdSe, ZnO, ZnS, CZTS, Cu2S, Bi2S3, Ag2S, HgTe, CdHgTe, InAs, InSb or any other suitable material);
  a piezoelectric material (such as Poly vinylidene fluoride (PVDF) ceramics such as Lead Zirconate Titanate (PZT), BaTiO3, ZnO, or any other suitable material);
  a pyro electric film (such as Poly vinylidene fluoride (PVDF), P(VDF-trifluoroethylene), ceramics such as LiTaO3, LiNbO3 or GaN or any other suitable material); or
  a biochemical species (Anti-Immunoglobulin G, antimicrobial peptides or any other suitable material).

The substrate or a layer between the substrate and the common conductive or semiconductive layer may be the functional layer. For instance, the substrate may comprise a pyroelectric ceramic such as $LiNbO_3$.

The step of receiving a plurality of sensors arranged in an array may include:
  forming the source electrode or drain electrode to provide a perimeter portion and at least one finger portion, the finger portion extending inwardly from the perimeter portion; and
  forming, for at least one of the sensors of the array, the other electrode of said at least one sensor into at least one finger portion which is interdigitated with the at least one finger portion of the source or drain electrode.

The step of applying a common conductive or semiconductive layer may include deposition or transfer of a conductive or semiconductive thin-film layer (e.g. graphene).

The above described steps of forming may comprise photolithography, or any other metal on substrate deposition technique.

The method may comprise:
  configuring read out circuitry to detect a sensed value of each sensor in the array using measurements of an electrical parameter of the source electrode and the drain electrode of each sensor.

The step of receiving a plurality of sensors arranged in the array may include:
  forming a first sense electrode extending between gate electrode and the drain electrode.

The method may comprise configuring the read-out circuitry:
  to detect a sensed value of each sensor in the array using measurements of one or more electrical parameters of the source electrode, the drain electrode and the first sense electrode of each sensor.

The step of receiving a plurality of sensors arranged in an array may include:
  forming a first sense electrode extending between the source electrode and the gate electrode and forming a second sense electrode extending between the gate electrode and the drain electrode.

The method may include configuring the read out circuitry to detect a sensed value of each sensor using measurements of one or more electrical parameters from the source electrode, the drain electrode, the first sense electrode and the second sense electrode for each sensor.

The step of applying a common conductive or semiconductive layer may include:
  applying the common conductive or semiconductive layer such that it is in electrical contact with the drain electrode, the source electrode, first sense electrode, and/or second sense electrode.

The method may include the step of configuring the read-out circuitry to either:

energise each sensor and read a sensed value sequentially; or energise the sensors simultaneously and read-out a sensed value sequentially; or energise the sensors simultaneously and read-out the sensed values simultaneously.

The steps of any method disclosed herein do not have to be performed in the exact order disclosed, unless explicitly stated or understood by the skilled person.

According to a further aspect, there is provided an apparatus, the apparatus comprising means for receiving a plurality of sensors arranged in an array, means for receiving a plurality of sensors arranged in an array, each sensor having a source electrode, a drain electrode and a channel, one of the source and the drain electrodes configured to receive a flow of charge carriers for injecting into the channel and the other configured to provide a current sink for said flow of charge carriers from the channel, wherein the source electrode and drain electrode are elongate and the channel has a channel width defined by the longitudinal extent of the source and/or drain electrode and a channel length defined by the separation between the source and drain electrodes;

means for applying a common conductive or semiconductive layer arranged to extend over the plurality of sensors of the array and configured to be in electrical contact with at least the source electrode and the drain electrode of each sensor; and wherein the source electrode or drain electrode of each sensor forms a substantially continuous sensor perimeter at least along the channel width which substantially encloses the other electrode of each sensor to inhibit the flow of charge carriers beyond the sensor perimeter to inhibit crosstalk between sensors in the array.

The present disclosure includes one or more corresponding aspects, examples or features in isolation or in various combinations whether or not specifically stated (including claimed) in that combination or in isolation. Corresponding means and corresponding functional units (e.g., object creator) for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:

FIG. 14 illustrates a flowchart according to a method of the present disclosure; and FIG. 15 illustrates schematically a computer readable medium providing a program.

DESCRIPTION OF EXAMPLE ASPECTS

Figure 1:
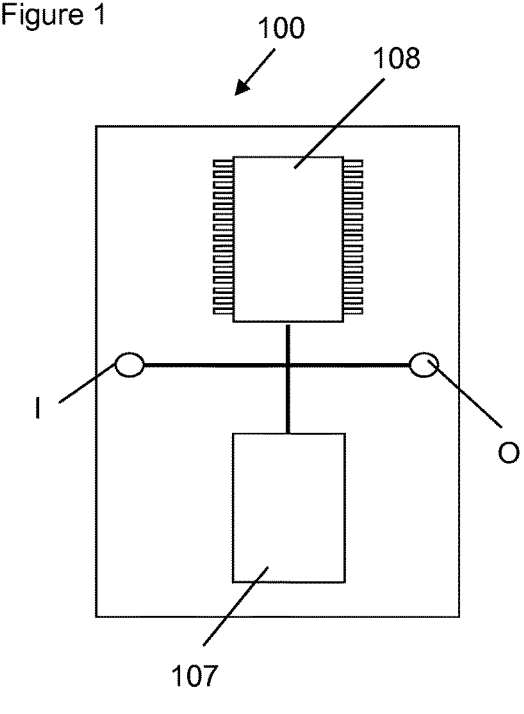
FIG. 1 illustrates an example apparatus embodiment comprising a number of electronic components, including memory and a processor, according to one embodiment of the present disclosure.

FIG. 1 shows an apparatus 100 comprising memory 107, a processor 108, input I and output O. In this embodiment only one processor and one memory are shown but it will be appreciated that other embodiments may utilise more than one processor and/or more than one memory (e.g. same or different processor/memory types).

In this embodiment the apparatus 100 is an Application Specific Integrated Circuit (ASIC) for an imaging device or sensor. In other embodiments the apparatus 100 can be a module for such a device, or may be the device itself, wherein the processor 108 is a general purpose CPU of the device and the memory 107 is general purpose memory comprised by the device.

The input I allows for receipt of signalling to the apparatus 100 from further components, such as the sensor array or the like. The output O allows for onward provision of signalling from within the apparatus 100 to further components. In this embodiment the input I and output O are part of a connection bus that allows for connection of the apparatus 100 to further components.

The processor 108 is a general purpose processor dedicated to executing/processing information received via the input I in accordance with instructions stored in the form of computer program code on the memory 107. The output signalling generated by such operations from the processor 108 is provided onwards to further components via the output O.

The memory 107 (not necessarily a single memory unit) is a computer readable medium (solid state memory in this example, but may be other types of memory such as a hard drive, ROM, RAM, Flash or the like) that stores computer program code. This computer program code stores instructions that are executable by the processor 108, when the program code is run on the processor 108. The internal connections between the memory 107 and the processor 108 can be understood to, in one or more example embodiments, provide an active coupling between the processor 108 and the memory 107 to allow the processor 108 to access the computer program code stored on the memory 107.

In this example the input I, output O, processor 108 and memory 107 are all electrically connected to one another internally to allow for electrical communication between the respective components I, O, 107, 108. In this example the components are all located proximate to one another so as to be formed together as an ASIC, in other words, so as to be integrated together as a single chip/circuit that can be installed into an electronic device. In other examples one or more or all of the components may be located separately from one another.

Figure 2:
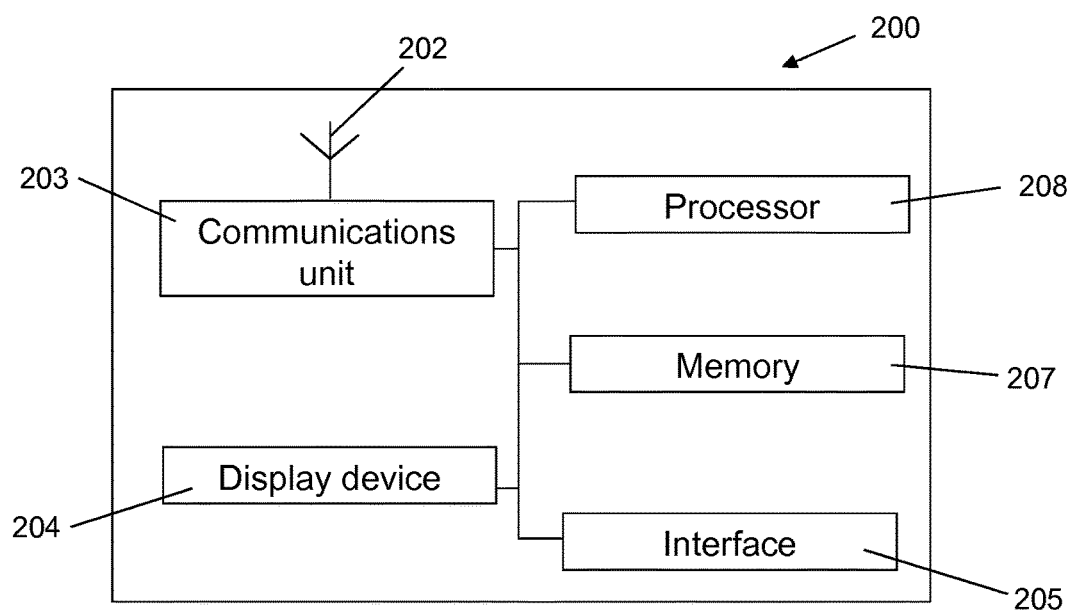
FIG. 2 illustrates an example apparatus embodiment comprising a number of electronic components, including memory, a processor and a communication unit, according to another embodiment of the present disclosure.

FIG. 2 depicts an apparatus 200 of a further example embodiment, such as an electronic device including a sensor array. In other example embodiments, the apparatus 200 may comprise a module for an electronic device and may just comprise a suitably configured memory 207 and processor 208.

The example embodiment of FIG. 2 comprises a display device 204 such as, for example, a liquid crystal display (LCD), e-Ink or touch-screen user interface. The apparatus 200 of FIG. 2 is configured such that it may receive, include, and/or otherwise access data. For example, this example embodiment 200 comprises a communications unit 203, such as a receiver, transmitter, and/or transceiver, in communication with an antenna 202 for connecting to a wireless network and/or a port (not shown) for accepting a physical connection to a network, such that data may be received via one or more types of networks. This example embodiment comprises a memory 207 that stores data, possibly after being received via antenna 202 or port or after being generated at the user interface 205. The processor 208 may receive data from the user interface 205, from the memory 207, or from the communication unit 203. It will be appreciated that, in certain example embodiments, the display device 204 may incorporate the user interface 205. Regardless of the origin of the data, these data may be outputted to a user of apparatus 200 via the display device 204, and/or any other output devices provided with apparatus. The processor 208 may also store the data for later use in the memory 207. The memory 207 may store computer program code and/or applications which may be used to instruct/enable the processor 208 to perform functions (e.g. read, write, delete, edit or process data).

Figure 3:
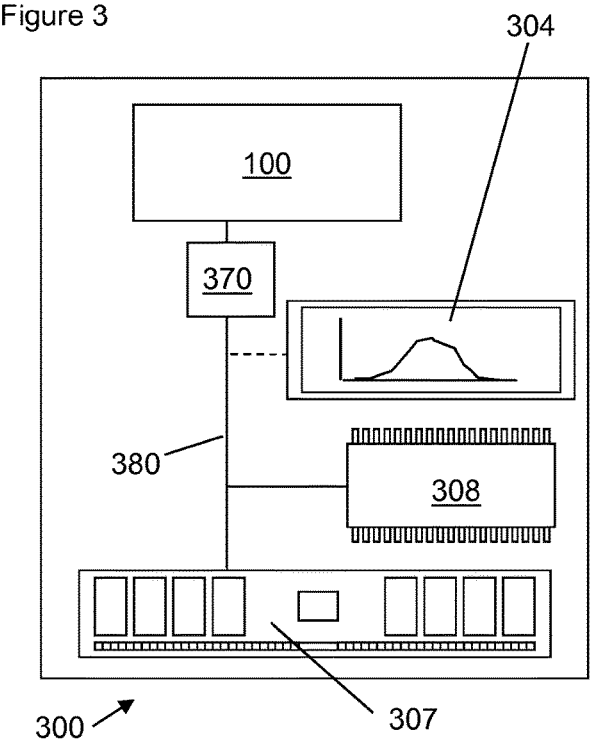
FIG. 3 illustrates an example apparatus embodiment comprising a number of electronic components, including memory and a processor, according to another embodiment of the present disclosure.

FIG. 3 depicts a further example embodiment of an electronic device 300, such as a tablet personal computer, a portable electronic device, a portable telecommunications device, a server or a module for such a device, the device comprising the apparatus 100 of FIG. 1. The apparatus 100 can be provided as a module for device 300, or even as a processor/memory for the device 300 or a processor/memory for a module for such a device 300. The device 300 comprises a processor 308 and a storage medium 307, which are connected (e.g. electrically and/or wirelessly) by a data bus 380. This data bus 380 can provide an active coupling between the processor 308 and the storage medium 307 to allow the processor 308 to access the computer program code. It will be appreciated that the components (e.g. memory, processor) of the device/apparatus may be linked via cloud computing architecture. For example, the storage device may be a remote server accessed via the internet by the processor. The device 300 may use a sensor array to detect a stimuli. The apparatus 100 in FIG. 3 is connected (e.g. electrically and/or wirelessly) to an input/output interface 370 that receives the output from the apparatus 100 and transmits this to the device 300 via data bus 380. Interface 370 can be connected via the data bus 380 to a display 304 (touch-sensitive or otherwise) that provides information from the apparatus 100 to a user. Display 304 can be part of the device 300 or can be separate. The device 300 also comprises a processor 308 configured for general control of the apparatus 100 as well as the device 300 by providing signalling to, and receiving signalling from, other device components to manage their operation.

The storage medium 307 is configured to store computer code configured to perform, control or enable the operation of the apparatus 100. The storage medium 307 may be configured to store settings for the other device components. The processor 308 may access the storage medium 307 to retrieve the component settings in order to manage the operation of the other device components. The storage medium 307 may be a temporary storage medium such as a volatile random access memory. The storage medium 307 may also be a permanent storage medium such as a hard disk drive, a flash memory, a remote server (such as cloud storage) or a non-volatile random access memory. The storage medium 307 could be composed of different combinations of the same or different memory types.

The present invention relates to an apparatus for sensing an external stimulus or stimuli using an array of sensors. The sensors of the array may define a sensing area. The apparatus 400 comprises an array of individual sensors 401 which can each measure a stimulus and, in combination, provide data which can represent the stimulus over the sensing area of the apparatus 400. The output of each sensor 401 may be one or more electrical signals. The combined output of the sensor array 402 may be received by an electronic device. The electronic device may be a digital camera, infrared camera, X-ray detector panel, biosensing platform, or the electronic device 300 may comprise a tablet personal computer, a portable electronic device, a portable telecommunications device, a server or a module for such a device, or a device comprising the apparatus 100 of FIG. 1 or apparatus 200 of FIG. 2, each arranged with the sensor array 402 or other embodiments thereof described therein.

The sensor array 402 may be configured to detect a desired type of stimulus by choosing an appropriate functional transducer layer to be applied to the sensor array 402. Stimuli for which the apparatus may be designed to measure may include, but are not limited to: temperature; motion; light; radiation; biological species; chemical species; etc. Thus, the material or form of the functional transducer layer may be selected to be sensitive to the desired stimulus. In other embodiments, the sensor array 402 does not include a functional transducer layer.

Figure 4:
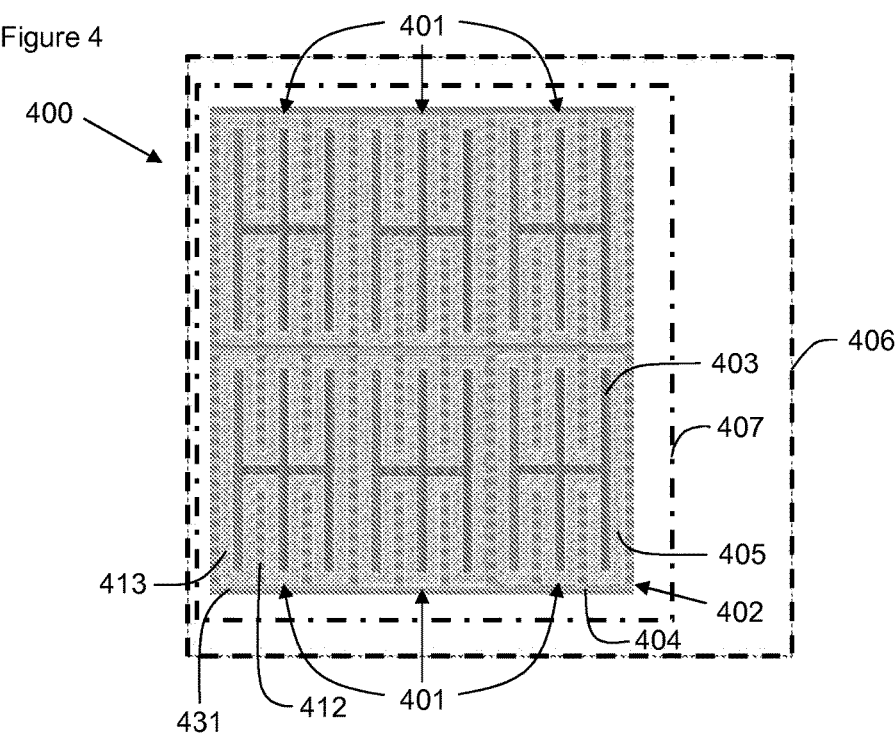
FIG. 4 illustrates an example apparatus including an array of sensors.

FIG. 4 illustrates an example embodiment of an apparatus 400 according to the present invention. The apparatus 400 comprises a plurality of sensors 401 arranged in an array 402. FIG. 4 shows six sensors 401 arranged in a 3×2 grid. Each sensor 401 in the array 402 comprises: a drain electrode 403, configured to receive a source of charge carriers; a source electrode 404, configured to provide a current sink for said flow of charge carriers; and a gate electrode 405 arranged to modulate the conductivity of the channel between the drain electrode 403 and source electrode 404. A common conductive or semiconductive layer 406, common to each of the sensors 401 in the array 402, is arranged to extend over the plurality of sensors of the array 402. The common conductive layer 406 is configured to be in electrical contact with at least the source electrode 404 and the drain electrode 403 of each sensor 401. In this example, the common conductive layer 406 is in direct electrical and physical contact with the drain and source electrode 403, 404. The source electrode 404 of each sensor 401 forms a substantially continuous perimeter which substantially encloses both the drain electrode 403 and the gate electrode 405 of each sensor to inhibit the flow of charge carriers from the drain electrode 403 beyond the source electrode 404 of each sensor 401 to inhibit crosstalk between sensors in the array 402. Thus, charge carriers introduced to the drain electrode 403 flow generally outwardly to the source electrode 404 located at the outer perimeter of each sensor. It will be appreciated by those skilled in the art that the charge carriers may be electrons or holes, depending which is the majority charge carrier for the particular implementation of the device. The substantially continuous arrangement of the source electrode 404 advantageously acts to prevent charge carriers leaking beyond the sensor perimeter that defines the area of each sensor 401, which is defined by the source electrode. The elongate source electrode forms a substantially continuous perimeter along the channel length and the channel width thereby wholly defining the sensor perimeter.

The common conductive layer 406 may be of any material which is suitable for sensing purposes (such as a thin film material). In the present invention the common conductive layer 406 is graphene. Graphene 406 may be damaged easily during device fabrication and so it is desirable to minimise the number of processing steps after the application of the graphene 406 to the apparatus 400.

The source electrode 404, drain electrode 403 and gate electrode 405 of each sensor 401 together with the graphene layer 406 (more generally, the common conductive or semiconductive layer) acting as the device channel, form a field effect transistor or transducer (FET). In a field effect transistor arrangement, the flow of charge carriers between the drain electrode 403 and the source electrode 404 is a function of the potential applied across the gate electrode 405. In the present invention, the conductive layer 406 forms at least part of a channel through which the charge carriers can diffuse between the source 404 and drain 403 electrodes.

The graphene layer 406 provides a region over which a field-sensitive layer can be formed between the source electrode 404 and the drain electrode 403 of each sensor 401. The graphene layer 406 also provides an interface which can be associated with a functional transducer layer 407. Graphene 406 is sensitive to changes in local electric fields and so functionalisation with any material which produces changes in the local electric field as a result of an external stimulus can provide for an effective functional transducer layer in combination with the graphene or other conductive layer.

In the embodiment of FIG. 4, the source electrode 404 is a common source electrode shared between at least two or more or all of the sensors in the array. The common source electrode 404 is configured to provide a common current sink for the flow of charge carriers applied to the respective drain electrode 403 of each sensor across the array 402. By using a common source electrode 404 to isolate the gate 405 and drain electrode 403 of each sensor from an adjacent sensor in the array, the source electrode 404 serves to inhibit crosstalk between the sensors in the array. In this apparatus, cross talk may refer to signals, electro-magnetic fields or charge carriers transmitted between sensors, which is typically disadvantageous.

Crosstalk may be reduced despite the use of a common conductive layer by designing the electrodes of the sensors 401 with appropriate geometries and, in particular, providing a current sink electrode as an outer boundary or substantially continuous perimeter between sensors.

It can be desirable to improve the width-to-length parameter of the channel of each sensor 401 geometry for advantageous performance and/or sensitivity. In order to achieve an improved width-to-length parameter, it may be desirable for the source electrode 404 to include one or more finger portions 412 which extend inwardly from the perimeter 431 substantially enclosing each sensor 401. Thus, the source electrode 404 may include a perimeter portion 431 and at least one finger portion 412 extending inwardly therefrom. The drain electrode 403 of at least one sensor 401 may also include at least one finger portion 413, complimentary to the finger portion 412, and which is interdigitated with the finger portion 412 of the source electrode 404. FIG. 4 shows a geometry in which the source electrode 404 provides four finger portions 412 per sensor 401 which extend inwardly from the source electrode perimeter 431 and interdigitate with finger portions 413 of the drain electrodes. The gate electrode 405, being positioned between the source electrode 404 and the drain electrode 403 may also include complimentary finger portions.

The source and drain electrode 403, 404 may be used to determine a sensed value from each sensor. For example, a voltage may be applied across the source and drain electrodes and the resultant current value may be measured.

Figure 5A:
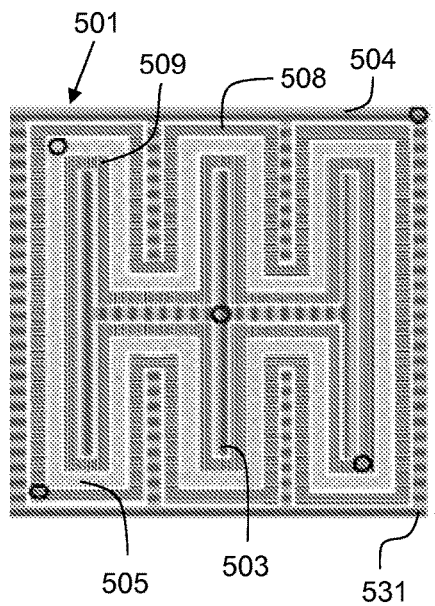
FIGS. 5a-5b illustrate a further apparatus including a sensor and an array of sensors.
Figure 5B:
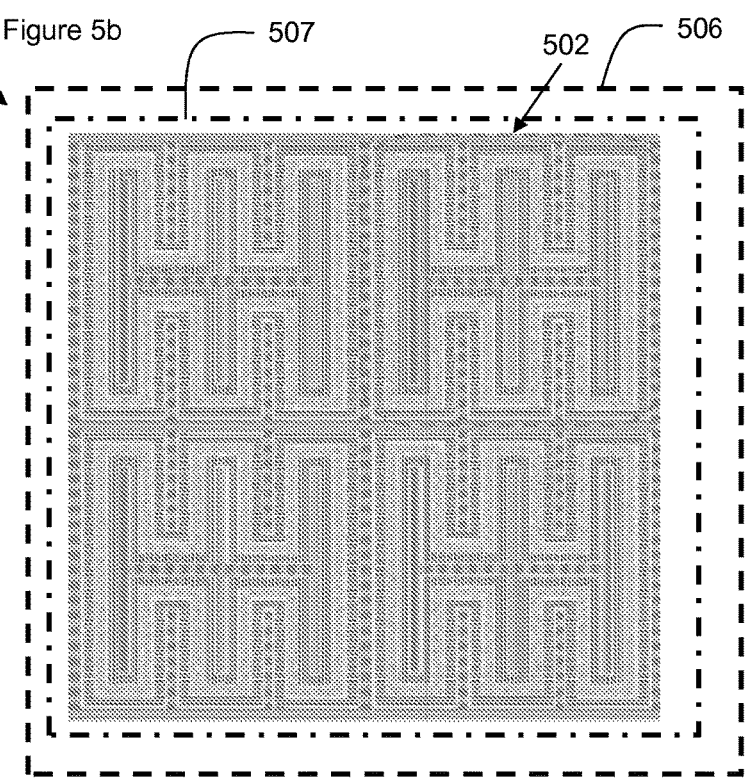

In a further embodiment, additional electrodes may be used to take readings from the sensors. In FIGS. 5*a* and 5*b* a further example apparatus 500, similar to that of FIG. 4 is shown which additionally includes a first sense electrode 508 and a second sense electrode 509. The sensor array 502 comprises a 2×2 array comprising four sensors 502. The first sense electrode 508 may be substantially enclosed by the source electrode 504. In this example the first sense electrode 508 is disposed between the source electrode 504 and the gate electrode 505. The second sense electrode 509 may be substantially enclosed by the gate electrode 505 wherein the second sense electrode 509 is disposed between the gate electrode 505 and the drain electrode 503.

The source electrode 504 of each sensor 501 in the array 502 is configured to form a substantially continuous perimeter 531 which substantially encloses the drain electrode 503. The common conductive layer 506 is configured to electrically contact the source, drain, first sense and second sense electrodes. The gate electrode is separated from the common conductive layer by a dielectric layer, which is described below in relation to FIG. 6.

Figure 6:
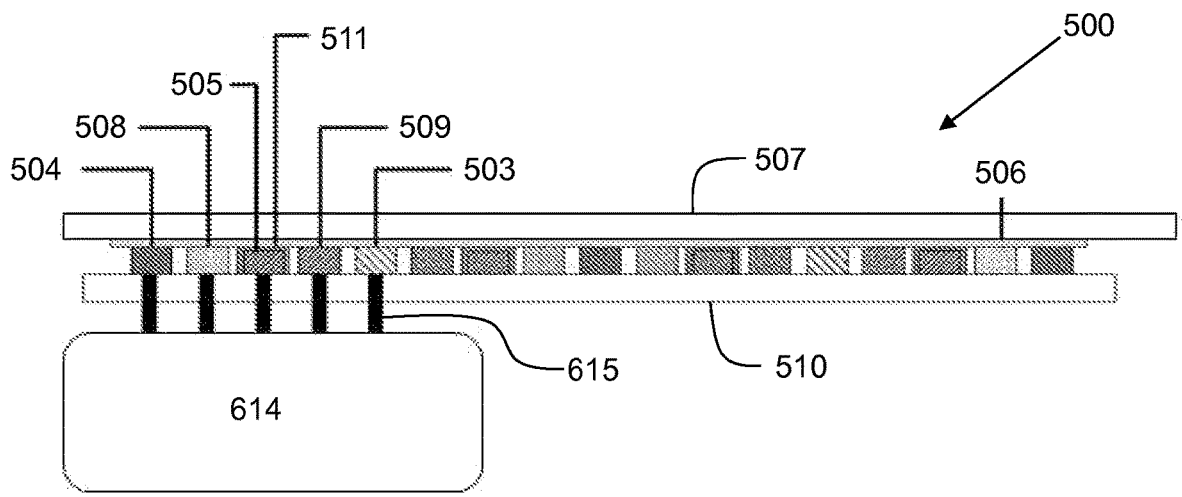
FIG. 6 illustrates a cross-sectional schematic diagram of a sensor arrangement.

FIG. 6 shows a cross-section through a sensor array that includes the first and second sense electrodes of FIG. 5*b*. The electrodes 503, 504, 505, 508, 509 may be formed in a substrate 510. The electrodes may be formed by any suitable conductor processing techniques such as by using CMOS or TFT technology. The graphene layer 506 may then be applied to the manufactured sensing array 502 for example by transfer techniques. After this, no further processing steps need to be applied to the apparatus 500, other than to possibly functionalise the graphene layer 506. It will be appreciated that the graphene layer 506 may be sensitive to certain stimuli without a functional transducer layer.

A dielectric material 511 is interposed between the gate electrode 505 and the common conductive layer 506. Application of a voltage at the gate electrode may generate an electric field that modulates the conductivity of the channel. As will be known to those skilled in the art the electric field acts to modulate the carrier concentration (and type) within the graphene channel. The electric field also controls the Fermi energy in the graphene. The source 504, drain 503, first sense 508 and second sense 509 electrodes are in direct electrical contact with the common conductive layer 506. They are also, in this embodiment, in direct physical contact.

It will be appreciated that substantially enclosing one electrode within another electrode is intended to mean that the electrode is enclosed when observed from a plan view and thus in the plane of the substrate 510. The electrode is not enclosed either above or below the plane of the substrate 510, as made clear in FIG. 6. Thus, the source electrode 405, 505 forms a substantially continuous perimeter 431, 531 in plan view.

The electrodes are connected to a read-out circuitry 614 by means of electrical connectors 615, such as vias. These electrical connectors 615 may extend substantially through the substrate 510 in which the electrodes 503, 504, 505, 508, 509 are formed. It will be appreciated that, while vias 615 have been provided as an example, any suitable connection to the read-out circuitry 614 may be used. One or more vias 615 are provided per electrode per sensor 501 for the source 404, gate 405 and drain 403 electrodes. In other examples which include one or more sense electrodes 508, 509, one or more vias may be provided for each sense electrode. In other embodiments any one of the electrodes may connect to the read-out circuitry by one or more vias 615.

The read-out circuitry 614 is configured to detect at least one electrical parameter from one or more or each sensor of the sensor array 502. The electrical parameter to be read out may be the sensor resistance or current or voltage.

Figure 7:
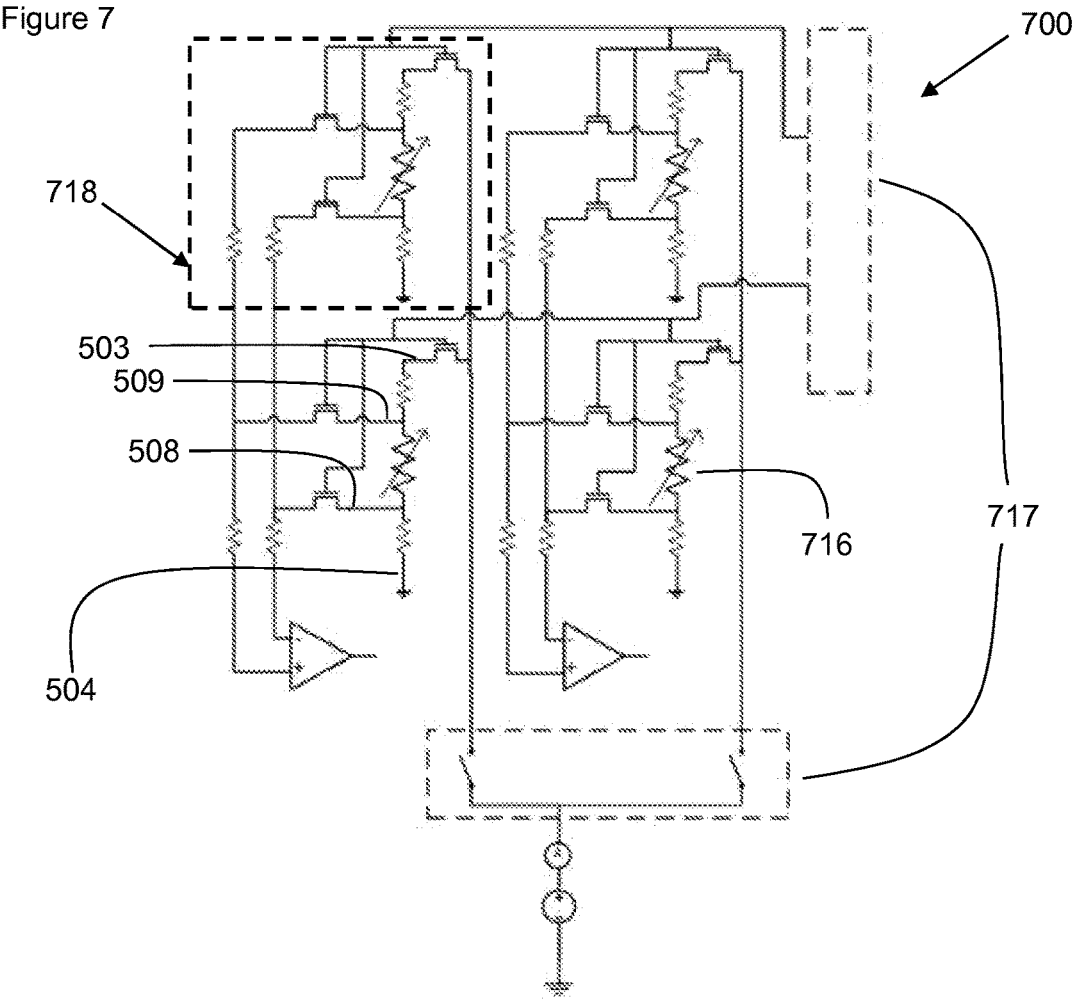
FIG. 7 illustrates an example read-out circuit for reading sensed values from the apparatus.

FIG. 7 shows example read-out circuit 700 for a 2×2 array of sensors 502 configured such that an electrical parameter may be measured and read from each sensor in sequence. The graphene-FET (GFET) configuration shown as an example in FIGS. 4 and 5 may be seen as a variable resistor 716 which is sensitive to whatever stimulus the graphene layer 507 has been functionalised to detect. Means are provided for row and column selection 717 in order to allow the selection of individual sensors 718, 501 for read-out. The read-out circuitry 700 is configured such that application of the appropriate row and column selection 717, causes the application of a voltage between the source and drain electrodes to provide a flow of charge carriers in the selected sensor. The voltage difference between the first sense electrode 508 and second sense electrode 509 is indicative of a sensed value in response to the stimuli.

Figure 8A:
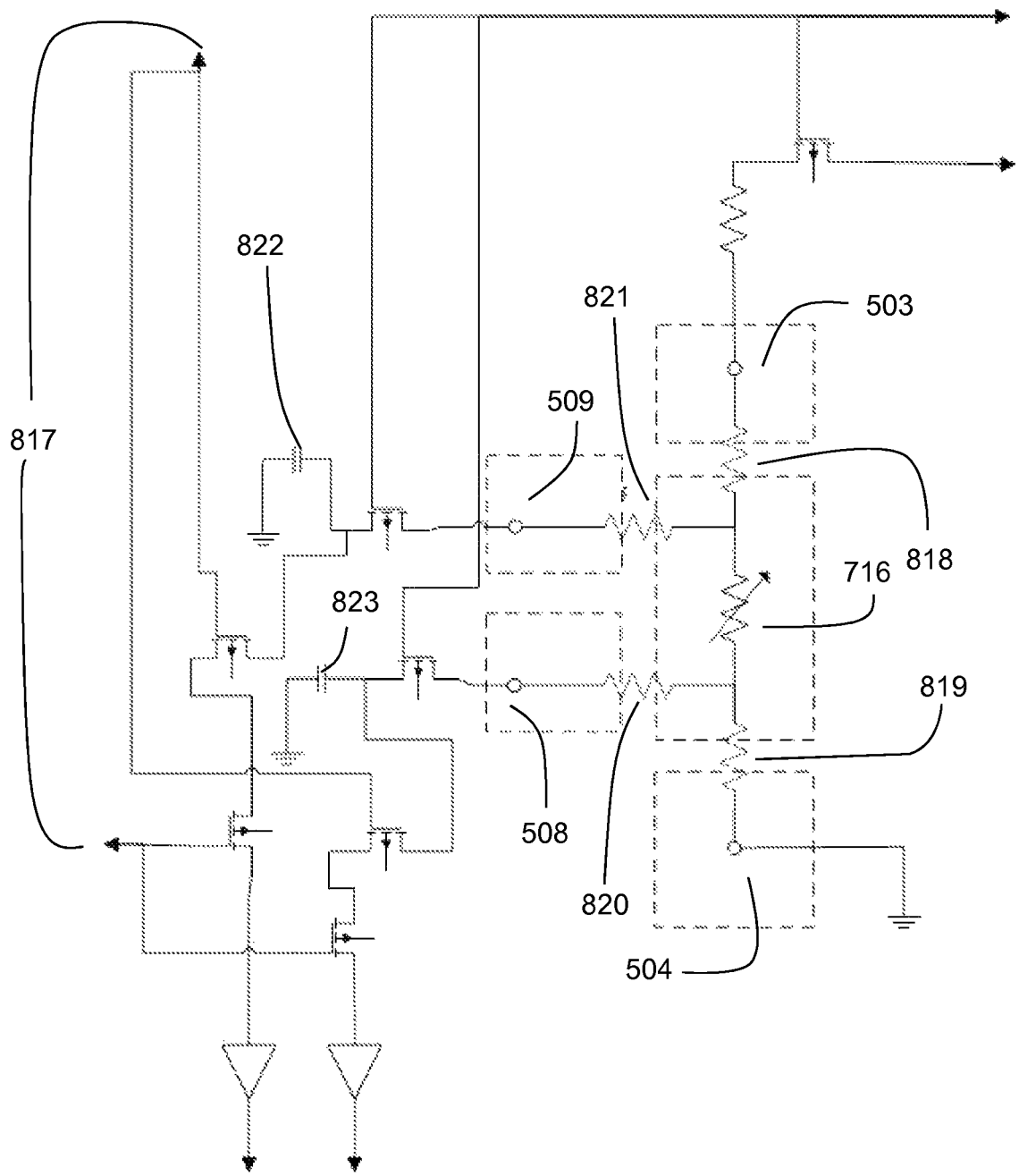
FIGS. 8a-8b illustrate further example read-out circuits for reading sensed values from the apparatus.
Figure 8B:
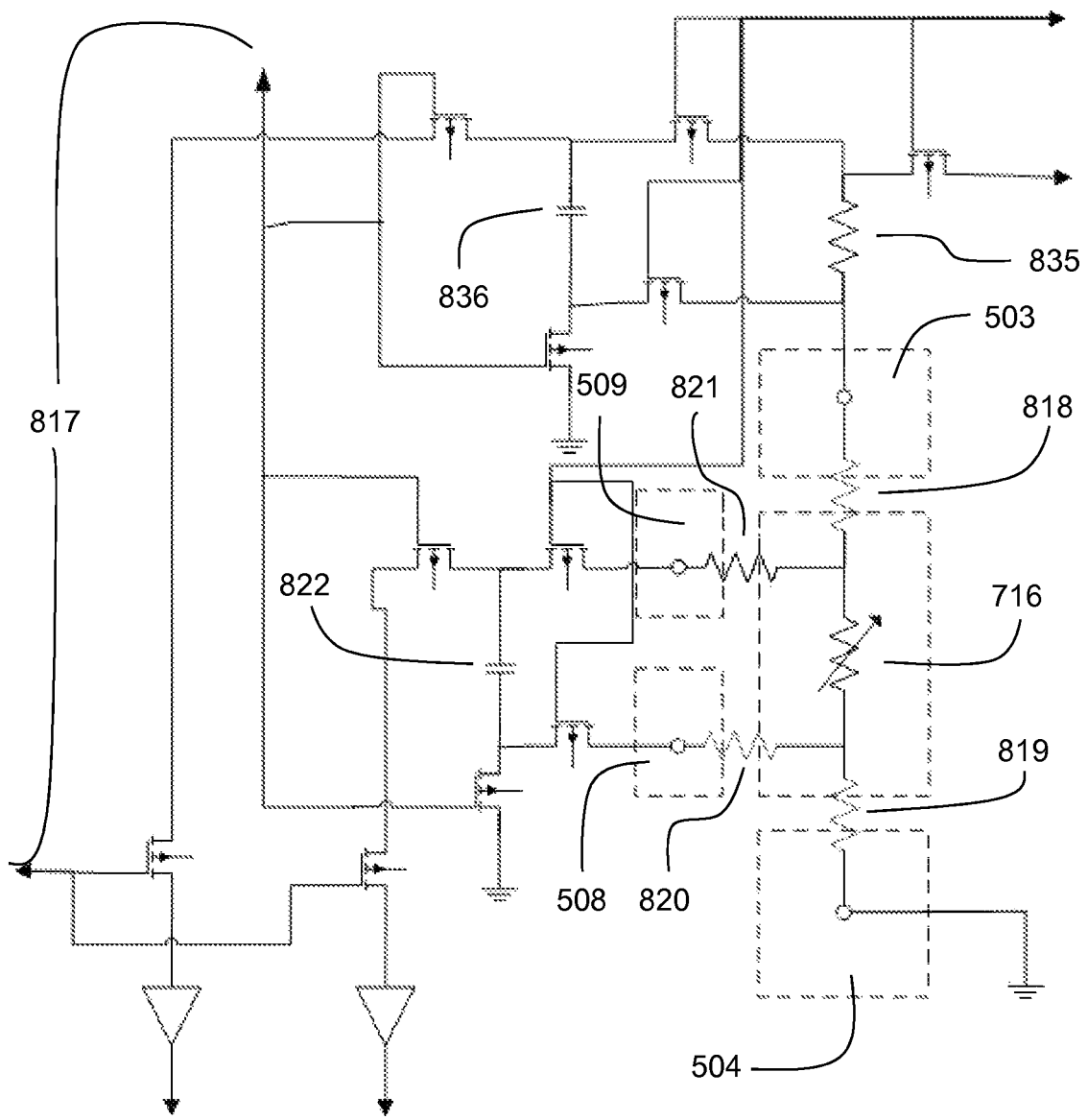

Alternatively, a sample-and-hold circuit configuration 800 may be used in order to read-out the sensed value of each sensor in the array 502. A sample-and-hold circuit 800 comprises a number of switching transistors and at least one storage capacitor. FIGS. 8a and 8b show part of the read-out circuit that is configured to be associated with a single sensor that uses two sense electrodes 508, 509 in addition to the source 504, gate 505 and drain 503 electrodes. The contact resistance of the source 504, drain 503, first sense 508 and second sense 509 electrodes interface to the common conductive layer 506 are shown diagrammatically as a resistors 818, 819, 820, 821 in the circuit diagram. The resistors are also representative of the inherent resistance of the vias.

In the configuration shown in FIG. 8a, each sensor 501 in the array is energised simultaneously by applying a voltage across the source and drain electrodes. Alternatively, each sensor 501 may be energised sequentially by applying a voltage across the source and drain electrodes of respective sensors in turn. Capacitors 822 and 823, which 'store' the sensed value, are then read sequentially by implementing means for row and column selection 817 of the sensors in the array 502. Thus, the sensed value is manifested as a voltage which is used to charge the capacitors 822 and 823. The charge on the capacitors can then be read out at a time they are selected.

FIG. 8b shows an alternative sample-and-hold circuit configuration which incorporates a reference resistor 835 of known resistance and a reference storage capacitor 836. Given a known value of vdd and the known reference resistor resistance, the voltage stored at the reference resistor 835 is indicative of the current through the GFET 716. In this embodiment, only a single capacitor 822 is associated with the read-out of the sensed value.

Figure 9A:
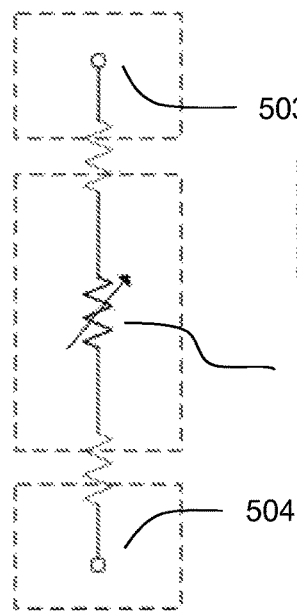
FIGS. 9a-9c illustrate examples of a two-point, three-point and four-point architecture contacting each of the sensors in the array for reading sensed values from the sensors.
Figure 9B:
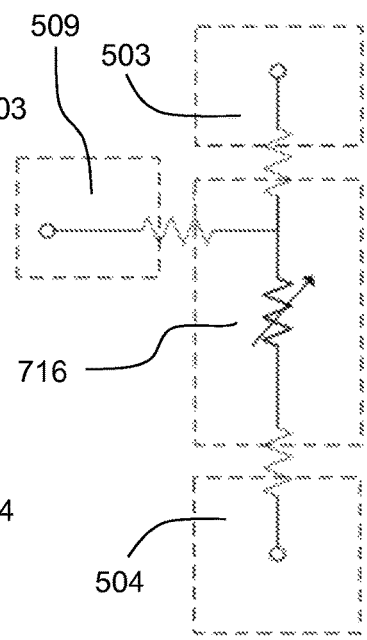
Figure 9C:
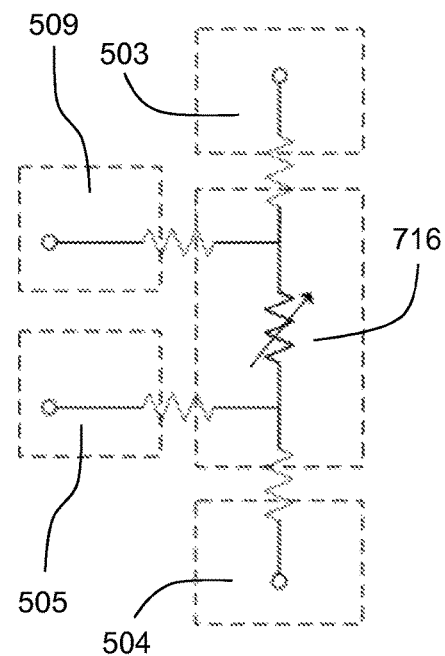

FIGS. 9a-9c show three variations of the FET structure shown in FIGS. 8a and 8b in which zero (two point architecture), one (three point architecture) and two (four point architecture) sense electrodes are used, respectively. In FIG. 9a, a current flow between the source and drain electrode may be indicative of a sensed value. In FIG. 9b, a voltage between the first sense and source electrodes may be indicative of the sensed value. In FIG. 9c a voltage between the first and second sense electrodes may be indicative of the sensed value.

Figure 10A:
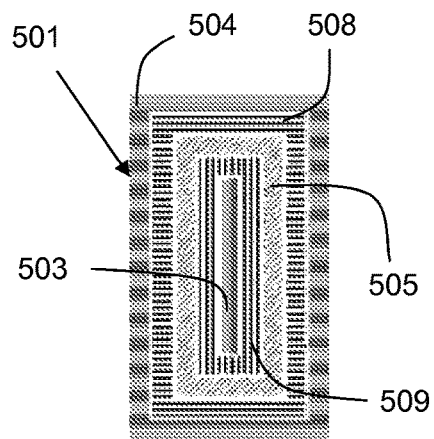
FIGS. 10a-10b illustrate a still further alternative example sensor and an array of sensors.
Figure 10B:
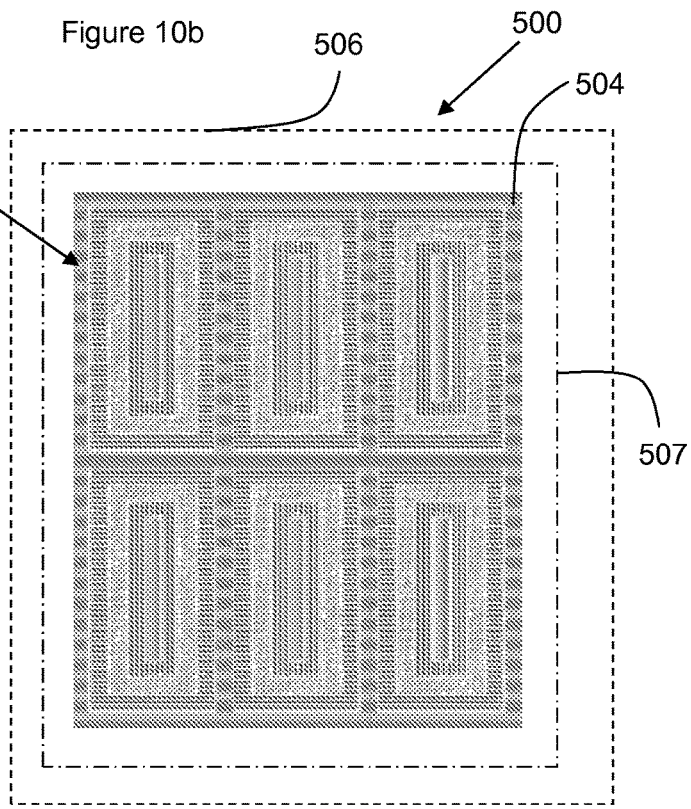

FIGS. 10a and 10b show an alternative embodiment of the apparatus 500 and sensor array 502 similar to that of FIGS. 5a and 5b and therefore the same reference numerals have been used. However, in this example, no finger portions are provided for any of the electrodes. FIG. 10a shows a single sensor element 501 whilst FIG. 10b shows a 3×2 array of such sensors 502 with a common source electrode 504. For each sensor 501, the source electrode 504 provides a wholly continuous perimeter. In this example, the source electrode 504 provides a common source electrode for each sensor 501 in the array of sensors 502. Thus, the common source electrode 504 acts to substantially prevent charge carriers from flowing to adjacent sensors. The elongate source electrode thus forms a wholly continuous perimeter of the sensor around the channel.

Figure 11:
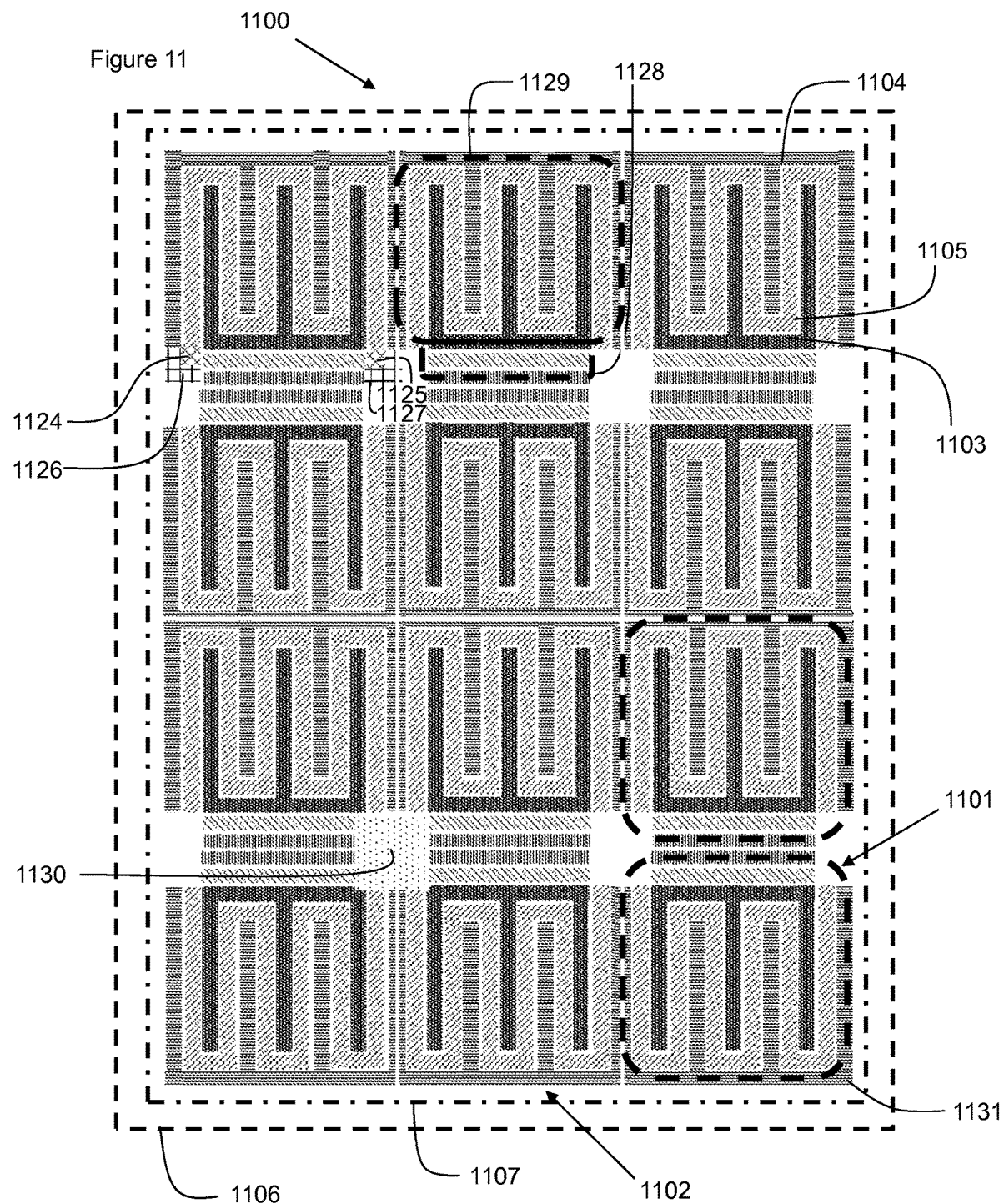
FIG. 11 illustrates an alternative example apparatus.

FIG. 11 shows an alternative embodiment of a sensor array. In this example each sensor 1101 includes a source electrode 1104, drain electrode 1103 and the gate electrode 1105. The source electrode 1104 is arranged to form a substantially continuous perimeter, substantially enclosing the gate 1105 and the drain 1103 electrode of each sensor 1101. A first source electrode break portion 1126 is provided per sensor 1101 in the sensor array 1102. A second source electrode break portion 1127 is provided per sensor 1101 in the sensor array 1102. The break portions comprise a break in the otherwise continuous perimeter provided by the source electrode 1104. The break portions extend across the channel length rather than the channel width, defined by the elongate nature of the source and drain electrodes. The gate electrode is arranged between the source and drain and, in this embodiment, a first gate electrode break portion 1124 is provided per sensor 1101 in the sensor array 1102. A second gate electrode break portion 1125 is provided per sensor 1101 in the sensor array 1102. In this configuration a continuous graphene layer 1106 is used as in the previous embodiments. In the regions where the source electrode is broken, the spacing between adjacent sensors is greater than regions where the source electrode is unbroken or continuous. In this example, the break portions are provided on one side of each sensor. On the side where the break portions are located, a spacing area 1130 in the substrate is provided between adjacent sensors. On the sides where the break portions are not present, the sensors are arranged such that they substantially abut one another and, specifically, do not include a spacing area 1130.

The break portions effectively split each sensor into two parts, each part comprising a graphene based field effect transistor. In particular, the gate break sections 1124, 1125 and the source break sections 1126, 1127 define a reference sensor part 1128 and a sensing sensor part 1129. Each reference sensor part 1128 has its own individual source electrode and each source electrode of the sensing sensor parts 1129 also has its own individual source electrode. All source electrodes are held at ground potential. When a voltage is applied across the source and drain electrodes, current flows in both the sensing sensor part and the reference sensor part. The current flowing to the drain is measured and the current flowing out from the reference sensor part 1128 source electrode is measured. This way, the resistance of both parts can be determined. The reference GFET is not functionalized and functions as a reference component, such as for temperature compensation.

Figure 12:
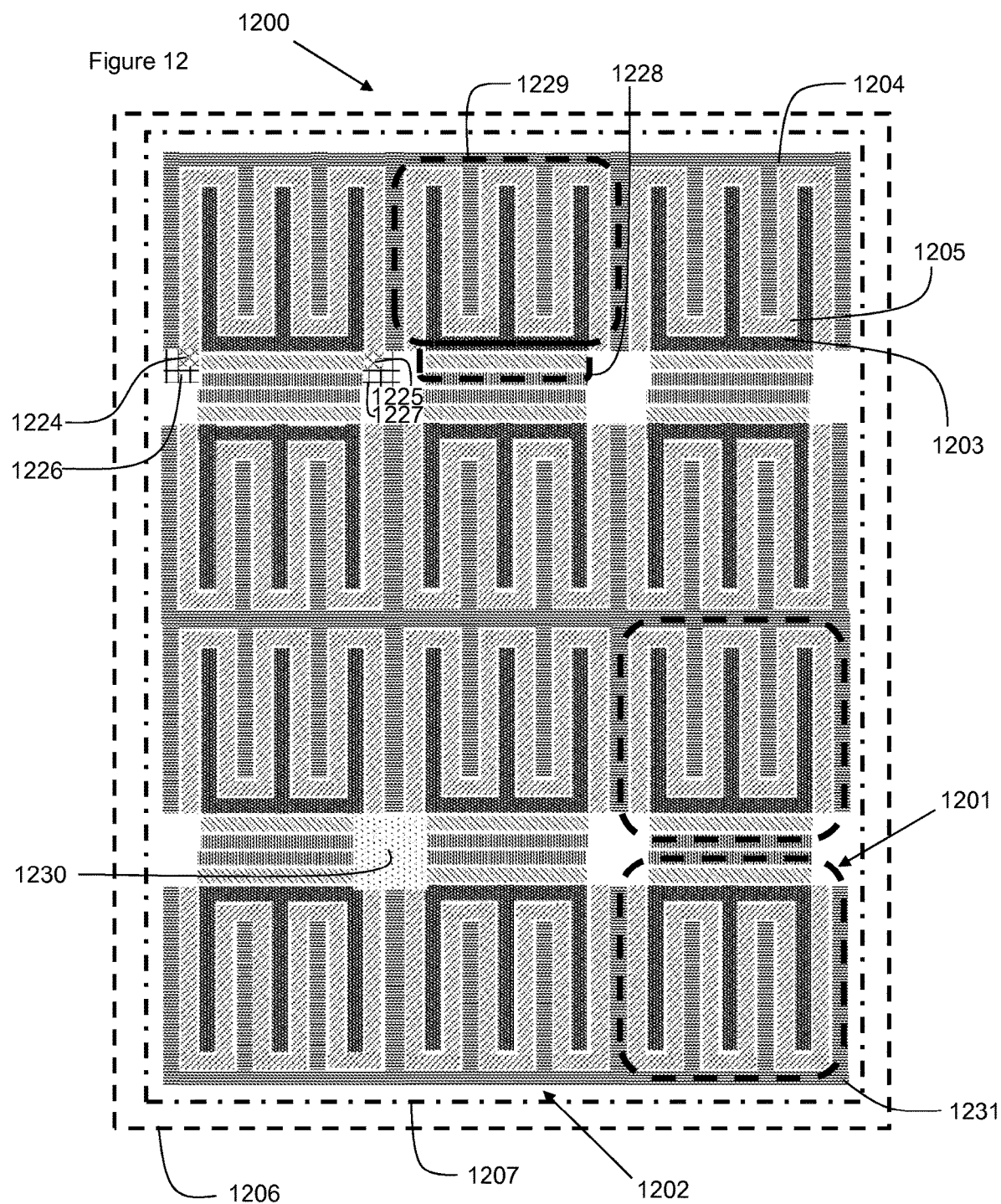
FIG. 12 illustrates an alternative example apparatus.

FIG. 12 shows an alternative embodiment of a sensor array 1200. In this example each sensor 1201 includes a source electrode 1204, a drain electrode 1203 and a gate electrode 1205. The source electrode 1204 is arranged to form a substantially continuous perimeter, substantially enclosing the gate 1205 and the drain 1203 electrode of each sensor 1201. A first source electrode break portion 1226 is provided per sensor 1201 in the sensor array 1202. A second source electrode break portion 1227 is provided per sensor 1201 in the sensor array 1202. The break portions comprise a break in the otherwise continuous perimeter provided by the source electrode 1204. The gate electrode is arranged between the source and drain electrodes and, in this embodiment, a first gate electrode break portion 1224 is provided per sensor 1201 in the sensor array 1202. A second gate electrode break portion 1225 is provided per sensor 1201 in the sensor array 1202. In this configuration a continuous graphene layer 1206 is used as in the previous embodiments. In the regions where the source electrode is broken, the spacing between adjacent sensors is greater than regions where the source electrode is unbroken or continuous. In this example, the break portions are provided on one side of each sensor. On the side where the break portions are located, a spacing area 1230 in the substrate is provided between adjacent sensors. On the sides where the break portions are not present, the sensors are arranged such that they substantially abut one another and, specifically, do not include a spacing area 1230.

The break portions effectively split each sensor into two parts, each part comprising a graphene based field effect transistor. In particular, the gate break sections 1224, 1225 and the source break sections 1226, 1227 define a reference sensor part 1228 and a sensing sensor part 1229. Each reference sensor part 1228 has its own individual source electrode whilst the source electrodes of the sensing sensor parts 1229 provide a common source between a subset of the sensors in the array. All source electrodes are held at ground potential. When a voltage is applied between the source electrode and the drain electrode, the current flows in both the sensing sensor part and the reference sensor part.

The current flowing in the sensing sensor part is measured and the current flowing in the reference sensor part 1228 source electrode is measured. This way, the resistance of both parts can be extracted. The reference GFET is not functionalized and functions as a reference component e.g. for temperature compensation.

Figure 13:
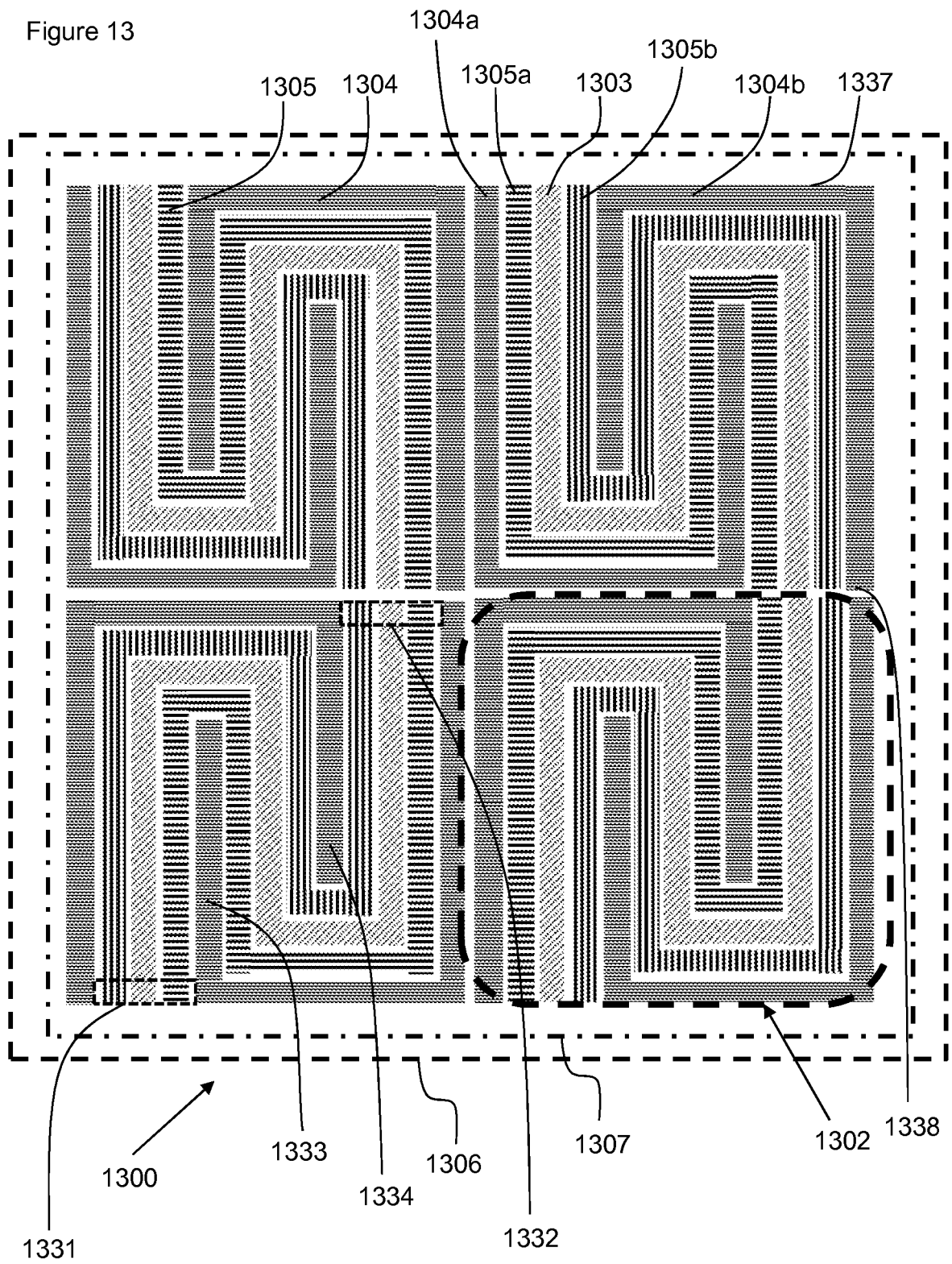
FIG. 13 illustrates an alternative example apparatus.

FIG. 13 shows an alternative embodiment of a sensor array 1300. In this example each sensor 1301 includes an elongate source electrode 1304, an elongate drain electrode 1303 and an elongate gate electrode 1305. The source electrode 1304 is arranged to substantially enclose the gate electrode 1305 and the drain electrode 1303 of each sensor 1301. The source electrode comprises a first source electrode break portion 1331 and a second source electrode break portion 1332. The break portions comprise a break in the otherwise continuous perimeter provided by the source electrode 1304. The source electrode additionally comprises a first finger portion 1333 and a second finger portion 1334. The first source electrode break portion 1331 is arranged substantially adjacent to the first finger portion 1333 and the second source electrode break portion 1332 is arranged substantially adjacent to the second finger portion 1334. The gate electrode 1305 and the drain electrode 1303 are arranged such that they extend within the first break portion 1331 and the second break portion 1332, such that they substantially fill the first break portion 1331 and the second break portion 1332. The arrangement of the first and second source electrode finger portions 1333, 1334 of each sensor 1301 and the first and second source electrode break portions 1331, 1332 of each sensor 1301 are arranged such that the gate electrode 1305 and the drain electrode 1303 of each sensor form a path which meanders through each sensor 1301. In this embodiment of the invention the source electrode 1304 of each sensor 1301 in the array is independent from the source electrode of the source electrode of each other sensor in the array. The source electrode 1304 of each sensor 1301 in the array does not form a common source electrode for each sensor in the array. For a sensor array comprising at least a first sensor and a second sensor, each having a meandering path arrangement, and wherein the second sensor is arranged substantially adjacent to an edge of the first sensor comprising a first or second break portion, the first or second break portion of the second sensor is arranged substantially adjacent to the break portion of the first sensor. An arrangement wherein the break portions of adjacent sensors are substantially adjacent to one another serves to reduce cross-talk between adjacent sensors compared to arrangements known in the art. Thus, the electrodes of each sensor element may face, at the sensor perimeter, a corresponding electrode of an adjacent sensor element. Accordingly, portions of the sensor perimeter that face an adjacent sensor element may be at substantially the same potential as a directly facing portion of the sensor perimeter of the adjacent sensor element.

The sensor elements of FIG. 13 are arranged in a grid of rows and columns and wherein the sensor elements in a common row (i.e. the top two sensor elements of FIG. 13) have a substantially identical layout and wherein sensor elements in a row adjacent to the common row (i.e. the bottom two sensor elements of FIG. 13) have a layout substantially a mirror image of the sensor elements in the common row.

Further, each of the electrodes and electrode parts are elongate members. The electrodes which form a first sensor in the array 1300 are discontinuous with the electrodes that form an adjacent sensor in the array. In this way, no common electrodes are provided between adjacent sensors in the array. The drain electrode 1303 is arranged to extend from a first side 1137 of its associated sensor to a second side 1338 of its associated sensor along a meandering path. Thus, the drain electrode 1303 may extend from a first side 1337 of its associated sensor element to a second side 1338 of its associated such that it has a plurality of changes in direction along its length prior to reaching the second side 1338 of its associated sensor. A first edge of the first gate electrode part 1305a extends along a first edge of the drain electrode 1303 such that the first gate electrode part 1305a extends from the first side 1337 of its associated sensor to the second side 1338 of its associated sensor. A first edge of the second gate electrode part 1305b extends along a second edge of the drain electrode 1303 such that the second gate electrode part 1305b extends from the first side 1337 of its associated sensor to the second side 1338 of its associated sensor. A first edge 1337 of the first source electrode part 1304a extends along a second edge 1338 of the first gate electrode part 1305a such that the first source electrode part 1304a extends from the first side 1337 of its associated sensor to the second side 1338 of its associated sensor. A first edge of the second source electrode part 1304b extends along a second edge of the second gate electrode part 1305b such that the second source electrode part 1304*b* extends from the first side 1337 of its associated sensor to the second side 1338 of its associated sensor.

Thus, in general, the source electrode comprises a plurality of sections that form a sensor perimeter around a meandering drain electrode, at least along the channel width defined by the longitudinal extent of the drain electrode.

FIG. 14 shows a flow diagram illustrating the steps of receiving a plurality of sensors arranged in an array 1402 and applying a common conductive or semiconductive layer over the substrate 1404. It will be appreciated that while the term "sensors" has been used to define the layout of the source electrode, drain electrode, gate electrode, optional sense electrodes and channel even though the assembly may only become capable of sensing one the common conductive or semiconductive layer is applied and any read-out circuitry is associated with the sensors. The step of receiving a plurality of electrodes 1402 may include forming the electrodes by any suitable conductor processing techniques such as by using CMOS or TFT technology and forming the channel, such as by doping a semiconductor substrate. The step of applying a common conductive layer 1404 may include transfer of a thin film that has been formed on a different substrate such as in the case of graphene, deposition of a thin film using vapour deposition techniques such as chemical vapour deposition, atomic layer deposition, physical vapour deposition, or could be formed from solution of substantially two-dimensional platelets using wet-coating, printing or Langmuir-Blodgett techniques. The method may include applying a functional transducer layer to the common conductive or semiconductive layer. The transducer layer may be applied by deposition methods such as wet-coating (spin coating, bar coating, spray coating), printing (inkjet printing, aerosol jet deposition, gravure printing, flexographic printing), or dry coating (thermal evaporation, sputter-coating).

The step of transferring graphene onto the sensor array may include, as an example only:
1. CVD growth of graphene on both surfaces of a metal catalyst foil such as copper foil
2. Coating one surface of the graphene/Cu foil with a protective polymer layer such as PMMA
3. Removing the graphene from the second surface of the graphene/Cu foil
4. Removing the copper by wet chemical etching, followed by cleaning and rinsing
5. Applying the protective layer/graphene while still wet to the target substrate and drying
6. Removing the protective layer using a solvent such as acetone or by thermal treatment
7. Thermally annealing the graphene on target substrate to improve adhesion.

The formation of the sensor array, field effect transistors and associated electrodes may be achieved by any appropriate conductor or semiconductor fabrication process, such as photolithography, which will be known to those skilled in the art. Further the application of the common conductive layer may be performed by any two-dimensional material handling process.

FIG. 15 illustrates schematically a computer/processor readable medium 1500 providing a program according to an example. In this example, the computer/processor readable medium is a disc such as a digital versatile disc (DVD) or a compact disc (CD). In other examples, the computer readable medium may be any medium that has been programmed in such a way as to carry out an inventive function. The computer program code may be distributed between the multiple memories of the same type, or multiple memories of a different type, such as ROM, RAM, flash, hard disk, solid state, etc. The computer/processor readable medium 1500 may include instructions for fabrication of the apparatus of FIG. 5, 6, 7, 8, 9, 9, 10, or 11.

The examples described above show the source electrode forming the "perimeter" of each sensor, although it will be appreciated that depending on the type of sensor element that is created, the drain electrode could alternatively form the "perimeter" and thereby surround the source electrode. Thus, the source and drain electrode of the above examples could be interchanged, as will be appreciated by those skilled in the art using the teachings of the present application.

The apparatus shown in the above examples may be included in a camera, x-ray detector, night vision goggles, portable electronic device, a laptop computer, a mobile phone, a Smartphone, a tablet computer, a personal digital assistant, a digital camera, a smartwatch, smart eyewear, a pen based computer, a non-portable electronic device, a desktop computer, a monitor, a household appliance, a smart TV, a server, or a module/circuitry for one or more of the same. Any device that requires a sensor array to process stimuli.

Any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some examples, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such examples can include a reduced requirement to download data when further functionality is required for a device, and this can be useful in examples where a device is perceived to have sufficient capacity to store such pre-programmed software for functionality that may not be enabled by a user.

Any mentioned apparatus/circuitry may have other functions in addition to the mentioned functions, and that these functions may be performed by the same apparatus/circuitry. One or more disclosed aspects may encompass the electronic distribution of associated computer programs and computer programs (which may be source/transport encoded) recorded on an appropriate carrier (e.g. memory, signal).

Any "computer" described herein can comprise a collection of one or more individual processors/processing elements that may or may not be located on the same circuit board, or the same region/position of a circuit board or even the same device. In some examples one or more of any mentioned processors may be distributed over a plurality of devices. The same or different processor/processing elements may perform one or more functions described herein.

The term "signalling" may refer to one or more signals transmitted as a series of transmitted and/or received electrical/optical signals. The series of signals may comprise one, two, three, four or even more individual signal components or distinct signals to make up said signalling. Some or all of these individual signals may be transmitted/received by wireless or wired communication simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/examples may consist of any such individual feature or combination of features. In view of the foregoing description it will be evident to a person skilled in the art that various modifications may be made within the scope of the disclosure.

While there have been shown and described and pointed out fundamental novel features as applied to examples thereof, it will be understood that various omissions and substitutions and changes in the form and details of the devices and methods described may be made by those skilled in the art without departing from the scope of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or examples may be incorporated in any other disclosed or described or suggested form or example as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus, comprising:
a plurality of electrode pairs arranged in an array, each electrode pair comprising a source electrode and a drain electrode; and
a common conductive or semiconductive layer arranged to extend over the plurality of electrode pairs of the array and configured to be in electrical contact with the source electrode and the drain electrode of each electrode pair to create an array of sensors,
wherein each sensor has a source electrode, a drain electrode, and a channel formed by part of the common conductive or semiconductive layer, wherein the source electrode and drain electrode are elongate, and the channel has a channel width defined by the longitudinal extent of the source or drain electrode and a channel length defined by the separation between the source and drain electrodes,
wherein the source electrode or drain electrode of each sensor forms a perimeter around the other electrode of each sensor,
wherein the common conductive or semiconductive layer is continuous and substantially unpatterned across the plurality of sensors, and
the common conductive or semiconductive layer consisting essentially of at least one layer of a two dimensional material selected from:
a single layer of a two dimensional material;
a bilayer of a two dimensional material; and
a plurality of layers of a two dimensional material.

2. The apparatus of claim 1 wherein the conductive or semiconductive layer is associated with a functional transducer layer.

3. The apparatus of claim 1, wherein each sensor includes a gate electrode arranged for modulating the conductivity of the channel between the drain electrode and the source electrode and a dielectric material is interposed between the gate electrode and the common conductive or semiconductive layer.

4. The apparatus of claim 1, wherein the source electrode or drain electrode that forms the perimeter comprises a common electrode for all or a subset of the sensors in the array.

5. The apparatus of claim 4 wherein the electrode that forms the perimeter is arranged as a grid configured to define the perimeter of each sensor in the array.

6. The apparatus of claim 3, wherein the source electrode, the gate electrode and the drain electrode of each sensor in the array are configured as part of a field effect transducer (FET).

7. The apparatus of claim 1, wherein the sensors are formed on a substrate and the common conductive layer or semiconductor layer is located on one side of the substrate and read-out circuitry, for reading the output of the sensors in the array, is
disposed on a second side of the substrate, opposed to the first side, and interconnected to the sensors via through-vias; or
disposed embedded in the substrate below the sensors and connected to the sensor electrodes; or
disposed on a separate substrate and connected to the sensor array by electrical connections.

8. The apparatus of claim 1, wherein the common conductive or semiconductive layer is graphene.

9. The apparatus of claim 2, wherein the functional transducer layer is selected from:
a layer of colloidal quantum dots encapsulated with ligands;
a layer of conductor or semiconductor nanocrystals;
a piezoelectric material;
a pyro electric film;
a biochemical species.

10. The apparatus of claim 3, wherein the source electrode comprises a perimeter portion and at least one finger portion, the finger portion extending inwardly from the perimeter portion; wherein
for at least one of the sensors of the array, either one of the drain electrode or the gate electrode of said at least one sensor is arranged to form at least one finger portion which is interdigitated with the at least one finger portion of the source electrode.

11. The apparatus of claim 7, wherein each sensor includes a gate electrode arranged for modulating the conductivity of the channel between the drain electrode and the source electrode and a dielectric material is interposed between the gate electrode and the common conductive or semiconductive layer, and wherein a first sense electrode extends between the source electrode and the gate electrode and a second sense electrode extends between the gate electrode and the drain electrode; and wherein the read out circuitry is configured to detect the sensed value of each sensor using measurements of an electrical parameter from the source electrode, the drain electrode, the first sense electrode and the second sense electrode for each sensor.

12. A method for forming an apparatus, comprising:
receiving a plurality of electrode pairs arranged in an array, each electrode pair comprising a source electrode and a drain electrode; and
applying a common conductive or semiconductive layer arranged to extend over the plurality of electrode pairs of the array and configured to be in electrical contact with at least the source electrode and the drain electrode of each electrode pair to create and array of sensors, wherein each sensor has a source electrode, a drain electrode, and a channel formed by part of the common conductive or semiconductive layer, wherein the source electrode and drain electrode are elongate, and the channel has a channel width defined by the longitudinal extent of the source or drain electrode and a channel length defined by the separation between the source and drain electrodes, wherein the source electrode or drain electrode of each sensor forms a perimeter around the other electrode of each sensor, wherein the common conductive or semiconductive layer is continuous and substantially unpatterned across the plurality of sensors, and the common conductive or semiconductive layer consisting essentially of at least one layer of a two dimensional material selected from:
a single layer of a two dimensional material;
a bilayer of a two dimensional material; and
a plurality of layers of a two dimensional material.

13. The method of claim 12 wherein following the step of applying the conductive or semiconductive layer, the method comprises:
applying a functional transducer layer to the common conductive or semiconductive layer.

* * * * *